US009539198B2

(12) United States Patent
Galdi et al.

(10) Patent No.: US 9,539,198 B2
(45) Date of Patent: Jan. 10, 2017

(54) PHOTOPROTECTION COMPOSITION CONTAINING HIGH LEVELS OF WATER-SOLUBLE UV FILTERS

(71) Applicant: L'OREAL, Paris (FR)

(72) Inventors: Angelike Galdi, Westfield, NJ (US); Andrew Goldberg, Clark, NJ (US); Catherine Chiou, Saddle Brook, NJ (US)

(73) Assignee: L'OREAL, Paris (FR)

( * ) Notice: Subject to any disclaimer, the term of this patent is extended or adjusted under 35 U.S.C. 154(b) by 188 days.

(21) Appl. No.: 14/136,562

(22) Filed: Dec. 20, 2013

(65) Prior Publication Data

US 2015/0174046 A1 Jun. 25, 2015

(51) Int. Cl.

| A61K 8/00 | (2006.01) |
|---|---|
| A61Q 17/04 | (2006.01) |
| A61K 8/891 | (2006.01) |
| A61K 8/46 | (2006.01) |
| A61K 8/893 | (2006.01) |
| A61K 8/894 | (2006.01) |
| A61K 8/06 | (2006.01) |

(52) U.S. Cl.
CPC .............. *A61K 8/891* (2013.01); *A61K 8/064* (2013.01); *A61K 8/466* (2013.01); *A61K 8/893* (2013.01); *A61K 8/894* (2013.01); *A61Q 17/04* (2013.01)

(58) Field of Classification Search
None
See application file for complete search history.

(56) References Cited

U.S. PATENT DOCUMENTS

| 4,268,499 | A | 5/1981 | Keil |
|---|---|---|---|
| 4,917,882 | A | 4/1990 | Strobridge |
| 5,601,811 | A | 2/1997 | Gallagher et al. |
| 6,524,598 | B2 | 2/2003 | Sunkel et al. |
| 6,696,049 | B2 | 2/2004 | Vatter et al. |
| 7,262,217 | B2 | 8/2007 | Baranger et al. |
| 8,216,555 | B2 | 7/2012 | Nieuwenhuijsen |
| 8,299,127 | B2 | 10/2012 | Anjing et al. |
| 8,461,206 | B2 | 6/2013 | Dalko |
| 8,481,594 | B2 | 7/2013 | Boulle et al. |
| 8,603,502 | B2 | 12/2013 | Boulle et al. |
| 8,609,117 | B2 | 12/2013 | Boulle et al. |
| 2003/0064046 | A1 | 4/2003 | Omura et al. |
| 2007/0128137 | A1 | 6/2007 | Yoshimi et al. |
| 2007/0264210 | A1 | 11/2007 | Robinson |
| 2009/0035236 | A1 | 2/2009 | Maes et al. |
| 2010/0179222 | A1 | 7/2010 | Boulle et al. |
| 2010/0310617 | A1 | 12/2010 | Zhang et al. |
| 2011/0256077 | A1 | 10/2011 | Hayakawa |
| 2012/0088836 | A1 | 4/2012 | Dalko |
| 2012/0322876 | A1 | 12/2012 | Kermorvan et al. |
| 2013/0142740 | A1 | 6/2013 | Cziryak et al. |
| 2013/0345317 | A1 | 12/2013 | Chiou |

FOREIGN PATENT DOCUMENTS

| CN | 1793822 | A | 6/2006 |
|---|---|---|---|
| EP | 1027883 | A2 | 8/2000 |
| EP | 1671680 | A1 | 6/2006 |
| EP | 1990372 | A2 | 11/2008 |
| FR | 2847469 | A1 | 5/2004 |
| FR | 2847470 | A1 | 5/2004 |
| FR | 2909552 | A1 | 6/2008 |
| FR | 2921254 | A1 | 3/2009 |
| FR | 2921255 | A1 | 3/2009 |
| FR | 2940053 | A1 | 6/2010 |
| FR | 2951375 | A1 | 4/2011 |
| FR | 2953718 | A1 | 6/2011 |
| FR | 2954122 | A1 | 6/2011 |
| FR | 2964865 | A1 | 3/2012 |
| FR | 2973693 | A1 | 10/2012 |
| FR | 2977478 | A1 | 1/2013 |
| FR | 2988291 | A1 | 9/2013 |
| FR | 2988292 | A1 | 9/2013 |
| JP | 2001205061 | A | 7/2001 |
| WO | 0069423 | A1 | 11/2000 |
| WO | 2010000584 | A2 | 1/2010 |
| WO | 2011054600 | A1 | 5/2011 |
| WO | 2012084699 | A2 | 6/2012 |
| WO | 2012084701 | A2 | 6/2012 |
| WO | 2012136564 | A2 | 10/2012 |
| WO | 2012136818 | A2 | 10/2012 |
| WO | 2012143645 | A2 | 10/2012 |
| WO | 2013007637 | A2 | 1/2013 |
| WO | 2013007647 | A1 | 1/2013 |
| WO | PCT/US2013/045613 | | 6/2013 |

OTHER PUBLICATIONS

C. Tran, J.F. Michelet, L. Simonetti, F. Fiat, A. Garrigues, A. Potter, E. Segot, R.E.B. Watson, C.E.M. Griffiths, O. De Lacharriere, In vitro and in vivo studies with tetra-hydro-jasmonic acid (LR2412) reveal its potential to correct signs of skin ageing, Journal of the European Academy of Dermatology and Venereology 2013 European Academy of Dermatology and Venereology, p. 1-9, DOI: 10.1111/jdv.12113.

M. Vonka, J. Kosek, Modelling the morphology evolution of polymer materials undergoing phase separation, Chemical Engineering Journal, 2012, p. 1-11, http://dx.doi.org/10.1016/j.cej.2012.06.091.

U.S. Appl. No. 14/136,471, filed Dec. 20, 2013, Chiou.

(Continued)

*Primary Examiner* — Nannette Holloman
(74) *Attorney, Agent, or Firm* — McNees Wallace & Nurick, LLC

(57) ABSTRACT

A water-releasing photoprotection composition in the form of an emulsion and process for preparing the photoprotection composition are provided. The photoprotection composition includes an aqueous phase and an oil phase. The aqueous phase includes at least one water-soluble UV filter. The oil phase includes dimethicone and an emulsifying crosslinked siloxane elastomer. The photoprotection composition has a phase ratio of the aqueous phase to the oil phase of from about 3 to about 12. The photoprotection composition converts from an emulsion to a plurality of droplets upon application of shear.

21 Claims, No Drawings

(56) References Cited

OTHER PUBLICATIONS

U.S. Appl. No. 14/136,634, filed Dec. 20, 2013, Chiou.
U.S. Appl. No. 14/136,714, filed Dec. 20, 2013, Chiou.
U.S. Appl. No. 13/529,059, filed Jun. 21, 2012, Abandoned, Chiou.
U.S. Appl. No. 13/855,495, filed Apr. 2, 2013, Chiou.

PHOTOPROTECTION COMPOSITION CONTAINING HIGH LEVELS OF WATER-SOLUBLE UV FILTERS

FIELD OF THE INVENTION

The present invention is directed to a sunscreen composition in the form of an inverse water-in-silicone emulsion containing high levels of water-soluble UV filters. The present invention also provides a water-releasing effect when applied onto a keratinous substrate such as skin, hair or nails. The water-releasing effect enables the composition, initially in the form of an emulsion, to be converted into a plurality of droplets upon application of shear such as, for example, rubbing.

BACKGROUND OF THE INVENTION

The photoprotection of keratinous substrates, especially skin, is considered by many to be necessary in order to facilitate protection from sunburn and photo-aging, as well as to decrease the chances of skin cancer development. There are typically two types of UV sunscreens used to accomplish photoprotection, namely, inorganic UV filters and organic UV filters.

Inorganic UV filters such as titanium dioxide and zinc oxide are typically employed in large quantities in order to ensure proper coverage/maximum protection over the surface onto which they are applied. As a result, they have a tendency to feel dry and impart an undesirable white color onto the treated surface.

Organic UV filters are typically classified as being either water-soluble or oil-soluble, based on their solubility. Oil-soluble UV filters, such as homosalate, octocrylene and avobenzone, while easy to incorporate into emulsions, often impart a greasy and tacky feeling onto a user's skin which consumers consider unpleasant and hence, undesirable.

Water-soluble UV filters do not impart this unpleasant feeling as they are considered by consumers to provide a much lighter skin feel. Water-soluble UV filters are often used in the form of a sodium salt (i.e., an electrolyte) in order to improve their solubility profile. The problem, however, is that such filters, due to their electrolytic properties, are difficult to formulate with when it comes to long-term stability. This lack of stability oftentimes manifests itself in the form of re-crystallization of the filters in the composition, causing them to separate from the emulsion. Additionally, water-soluble UV filters tend to have a detrimental effect on any thickener ingredients conventionally found in topical products as they too have a tendency to separate from the emulsion due to the electrolytic properties of the UV filters. As a result, water-soluble UV filters present a challenge for incorporation into emulsions intended for topical application onto a keratinous substrate, as most traditional emulsions are thickened and/or stabilized with natural or synthetic polymers such as gums and polyacrylates, which are very sensitive to electrolytes.

Therefore, it is an object of the present invention to provide a photoprotection composition containing at least one water-soluble UV filter, in a salt or an acid form, having improved stability but without having a greasy and/or tacky feel.

BRIEF DESCRIPTION OF THE INVENTION

All numbers expressing quantities of ingredients and/or reaction conditions are understood as being modified in all instances by the term "about", unless otherwise stated.

In general, the present invention is directed to an inverse water-in-oil (silicone) emulsion type photoprotection composition containing an emulsifying crosslinked siloxane elastomer and water-soluble UV filters (WSUVF).

It has been surprisingly discovered by the inventors that the stability problems encountered by the use of water-soluble UV filters in emulsions can be mitigated by the use of an inverse water-in-oil emulsion, where the WSUVFs are incorporated into the dominant water phase prior to emulsification. Such an approach fully solubilizes the WSUVFs and their salts and provides the emulsion stability without the use of any water phase thickeners. Furthermore, the oil (silicone) external phase gives the composition a pleasant, silky feel upon topical application.

In an exemplary embodiment, a photoprotection composition in the form of a stable, tactilely pleasing emulsion is provided. The composition includes an aqueous phase and an oil phase. The aqueous phase contains at least one water-soluble UV sunscreen filter, including its salt and/or acid form, at a concentration of from about 2% to about 25% by weight, based upon the total weight of the composition. The oil phase contains dimethicone at a concentration by weight of from about 1% to about 25%, based upon the total weight of the composition, and an emulsifying crosslinked siloxane elastomer at a concentration by weight of from about 0.5% to about 7%, based upon the total weight of the composition. The photoprotection skin care composition has a phase ratio of aqueous phase to oil phase of from about 3 to about 12. The photoprotection composition converts from an emulsion to a plurality of droplets upon application of force such as, for example, rubbing with one's fingers or using an electromechanical force-imparting device such as, for example, an electromechanical cleansing brush.

In another exemplary embodiment, a method of inhibiting UV rays from contacting keratinous substrates is provided. The method includes applying the above-disclosed photoprotection composition onto the surface of a keratinous substrate, followed by application of force onto the composition present on the keratinous substrate.

Other features and advantages of the present invention will be apparent from the following more detailed description of the preferred embodiment which illustrates, by way of example, the principles of the invention.

DETAILED DESCRIPTION OF THE INVENTION

"Keratinous substrate," as used herein, includes but is not limited to skin, hair, and nails.

"Force", as used herein, includes shear/friction produced by a rubbing motion of an end user's fingers, an electromechanical cleansing device having a movable brush with bristles, and/or an electromechanical device that produces a tapping motion, similar to one's fingers tapping on the surface of the skin.

"Homogenous" means substantially uniform throughout, i.e., a single phase mixture.

In the present application the term "ambient temperature" means a temperature of about 25° C.

In the present application the term "water-releasing," as used herein, describes the phenomenon wherein, after application of a photoprotection composition onto a target substrate, force is then applied onto the composition causing the water-in-oil type emulsion to rupture, which in turn causes the internal aqueous phase containing the water-soluble UV filters to emerge in the form of droplets.

The photoprotection composition and method of the present invention can comprise, consist of, or consist essentially of the essential elements and limitations of the invention described herein, as well as any additional or optional ingredients, components, or limitations described herein or otherwise useful in compositions intended for topical application onto keratinous substrates.

One advantage of an embodiment of the present disclosure includes providing a stable photoprotection composition capable of carrying relatively high levels of water-soluble UV filters without undergoing phase separation, i.e. re-crystallizing and/or breaking the emulsion. Yet another advantage of an embodiment of the present disclosure is providing a photoprotection composition capable of producing a water-releasing effect onto a keratinous substrate, such as skin. The water-releasing effect enables the composition, initially in the form of an emulsion, to be converted into a plurality of droplets carrying high levels of water-soluble UV filters upon application of force such as, for example, shear caused by an end user's rubbing of the composition onto the surface of a target keratinous substrate.

The water-in-oil emulsion system of the present invention typically has a white, glossy cream appearance. However, it may be modified so as to have a transparent gel-like or matte appearance by adjusting its refractive index. When the photoprotection composition is deposited onto a target keratinous substrate, followed by application of force, the composition quickly releases the aqueous phase containing the water-soluble UV filters in the form of bead-like droplets, thereby enabling the water-soluble UV filters present in the aqueous phase to be spread onto the surface of the target keratinous substrate.

Aqueous Phase

The aqueous phase present in the photoprotection composition according to the disclosure includes at least one water-soluble UV filter, water, and other aqueous phase ingredients. The aqueous phase of the photoprotection composition is at a concentration by weight of from about 60% to about 92%, or alternatively from about 70% to about 90%, or alternatively from about 80% to about 90%, based upon the weight of the photoprotection composition.

Water-Soluble Photoprotection Ingredient

The aqueous phase present in the photoprotection composition according to the disclosure includes at least one water-soluble UV filter at a concentration by weight of from about 2% to about 25% by weight, such as from about 3% to about 20% by weight, such as from about 4% to about 18% by weight, such as from about 4% to about 15% by weight, such as from about 5% to about 10% by weight, all weights based upon the weight of the composition.

Suitable examples of water-soluble UV filters that may be used include, but are not limited to, terephthalylidene dicamphor sulfonic acid (Ecamsule), phenylbenzimidazole sulfonic acid (Ensulizole), Benzophenone-4, aminobenzoic acid (PABA), 4-Bis(polyethoxy)-para-aminobenzoic acid polyethoxyethyl ester (PEG-25 PABA), camphor benzalkonium methosulfate, methylene bis-benzotriazolyl tetramethylbutylphenol (Bisoctrizole), disodium phenyl dibenzimidazole tetrasulfonate (Bisdisulizole disodium), and tris-biphenyl triazine; their derivatives and corresponding salts; naphthalene bisimide derivatives such as those described in European patent application EP1990372 A2, the entire contents of which is hereby incorporated by reference; and cinnamido amine cationic quaternary salts and derivatives such as those described in U.S. Pat. No. 5,601,811, the entire contents of which is hereby incorporated by reference, and mixtures thereof.

The salts of the compounds that may be used according to the invention are chosen in particular from salts of alkali metals, for example sodium or potassium; salts of alkaline-earth metals, for example calcium, magnesium or strontium; metal salts, for example zinc, aluminium, manganese or copper; salts of ammonium of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts. Salts chosen from sodium, potassium, magnesium, strontium, copper, manganese or zinc salts are preferably used. The sodium salt is preferentially used.

In general, any WSUVF capable of absorbing UV light in the range of from about 280 to about 400 nm can be employed in the present invention.

Water

The aqueous phase present in the photoprotection composition according to the disclosure includes water at a concentration by weight of about 60% to about 92%, or alternatively about 70% to about 90% or alternatively about 80% to about 90%, based upon the total weight of the composition. The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of thermal water.

Oil Phase

The oil phase present in the photoprotection composition according to the disclosure includes dimethicone and an emulsifying crosslinked siloxane elastomer. The oil phase of the water-releasing photoprotection composition is at a concentration by weight of about 8% to about 25%, or alternatively about 10% to about 20%, or alternatively about 10% to about 15%, based upon the total weight of the photoprotection composition.

Dimethicone

The oil phase present in the photoprotection composition according to the disclosure includes dimethicone at a concentration, by weight, of about 1% to about 25%, or alternatively about 2% to about 20%, or alternatively about 4% to about 15%, based upon weight of the composition.

Emulsifying Crosslinked Siloxane Elastomer

The oil phase present in the photoprotection composition according to the disclosure includes an emulsifying crosslinked siloxane elastomer at a concentration, by weight, of about 0.1% to about 20%, or alternatively about 0.3% to about 10%, or alternatively about 0.5% to about 7%, based upon weight of the composition.

Examples of suitable emulsifying crosslinked siloxane elastomers, include, but are not limited to, substituted or unsubstituted dimethicone/copolyol crosspolymer, dimethicone and dimethicone/PEG-10/15 crosspolymers, substituted or unsubstituted dimethicone/polyglyceryl crosspolymer, dimethicone and dimethicone/polyglycerin-3 crosspolymer. Such suitable emulsifying crosslinked siloxane elastomers are sold or made, for example, under the names of "KSG-210" a polyether-modified crosspolymer with an INCI name of dimethicone (and) dimethicone/PEG-10/15 crosspolymer, and "KSG-710" a polyglycerin-modified crosspolymer with an INCI name of dimethicone (and) dimethicone/polyglycerin-3 crosspolymer, both available from Shin-Etsu Silicones of America, Inc. (Akron, Ohio).

Co-Emulsifier

The oil phase present in the photoprotection composition according to the disclosure may optionally include a co-emulsifier at a concentration by weight of about 0.01% to about 5%, or alternatively about 0.05% to about 3%, or alternatively about 0.07% to about 1%, based upon the total weight of the composition. If the co-emulsifier concentration exceeds 1% by weight of the photoprotection composition, then the photoprotection composition may still form an emulsion but the desirable transformative effect of cream changing to droplets upon application of shear is not achieved.

Suitable examples of co-emulsifiers include polyether substituted linear or branched polysiloxane copolymers. One preferred co-emulsifier is PEG-10 dimethicone available under the tradename of ES-5612 from Dow Corning Corporation (Midland, Mich.), or KF-6017 from Shin-Etsu (Akron, Ohio). Another preferred co-emulsifier is dimethicone (and) PEG/PPG-18/18 dimethicone available under the tradename of ES-5226 DM from Dow Corning Corporation (Midland, Mich.). Other suitable co-emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio). Another suitable example of a co-emulsifier is polyoxyalkylene copolymers also known as silicone polyethers. Polyoxyalkylene copolymers are described in detail in U.S. Pat. No. 4,268,499, which is incorporated herein by reference in its entirety. A particularly preferred polyoxyalkylene copolymer is known by its CTFA designation as dimethicone copolyol. A particularly preferred form of dimethicone copolyol is supplied by Dow Corning as DC5225C.

Optional Powders

The photoprotection composition of the present disclosure may optionally include powders. The optional powders provide formulas that are smoother and softer on the skin. Representative powders include, but are not limited to talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. A representative powder includes, for example, polymethylsilsesquioxane. Powders may be present in the compositions in amounts generally ranging from about 0.1% to about 5% by weight, based on the total weight of the composition.

Phase Ratio

The phase ratio is calculated by dividing the total weight of the aqueous phase by the total weight of the oil phase. The photoprotection composition of the present disclosure as a water-in-oil emulsion has a ratio by weight of the aqueous phase to oil phase of from about 3 to about 12, or alternatively about 4 to about 10, or alternatively about 5 to about 9. The phase ratio excludes any additional optional powders that may be added to the composition. Without intending to be bound by theory, this phase ratio is believed to be critical to: (1) the stability of the emulsion in view of the high concentration of water-soluble UV sunscreen filters contained therein, and (2) the formation of droplets upon application of force onto the emulsion.

Water-Releasing Effect

With respect to the present invention, a good water-releasing effect of the water-in-oil emulsion means that the water-releasing effect has an evaluation result of more than or equal to a score of 3 in the evaluation system described below. The test method and evaluation score of the test system are described below.

About 0.2 g of a water-in-oil emulsion sample of cosmetic composition is taken and placed on the back of a hand, then it is applied thereon by circling gently with the middle finger and ring finger of the other hand, and then the phenomenon of the water-releasing effect is observed when the circling application reaches 20 cycles, and evaluated by a 5-level scoring system. A score of 5 represents that more than 10 bead-like water drops having an average diameter of more than or equal to 3 mm appear, or more than 20 bead-like water drops having an average diameter of more than or equal to 1 mm appear. A score of 4 represents that 2-10 bead-like water drops having an average diameter of more than or equal to 3 mm appear, or 10-20 bead-like water drops having an average diameter of more than or equal to 1 mm appear and the bead-like water drops having an average of more than or equal to 3 mm are no more than 10. A score of 3 represents that 2-9 bead-like water drops having an average diameter of more than or equal to 1 mm appear and there is at most 1 bead-like water drop having an average diameter of more than or equal to 3 mm, or 10-20 bead-like water drops having an average diameter of 1 mm appear. A score of 2 represents that 2-9 bead-like water drops having an average diameter of 1 mm appear. A score of 1 represents that no water drop appears. Each level between scores 5 to 4, 4 to 3, 3 to 2, and 2 to 1 shows that the water-releasing effect is between the two end values described above, and the lower the score, the poorer the water-releasing effect.

In one embodiment, the water-releasing effect of the cosmetic composition of the present disclosure is about 3 to 5.

EXAMPLES

TABLE 1

| | | Examples 1-5 (Inventive) | | | | |
|---|---|---|---|---|---|---|
| Phase | US INCI Name | Ex. 1 | Ex. 2 | Ex. 3 | Ex. 4 | Ex. 5 |
| A | DIMETHICONE | 7 | 7 | 7 | 6 | 6 |
| A | DIMETHICONE (and) DIMETHICONE/PEG-10/15 CROSSPOLYMER [KSG-210] | 5 | 5 | | 6 | 6 |

TABLE 1-continued

Examples 1-5 (Inventive)

| Phase | US INCI Name | Ex. 1 | Ex. 2 | Ex. 3 | Ex. 4 | Ex. 5 |
|---|---|---|---|---|---|---|
| A | DIMETHICONE (and) DIMETHICONE/POLYGLYCERIN-3 CROSSPOLYMER [KSG-710] | | | | 5 | |
| B1 | WATER, PRESERVATIVES | 53.21 | 56.87 | 56.87 | 46.41 | 37.15 |
| B1 | GLYCERIN | 15 | 15 | 15 | 15 | 15 |
| B1 | PROPANEDIOL | 3 | 3 | 3 | 3 | 3 |
| B1 | SODIUM CHLORIDE | 0.5 | 0.5 | 0.5 | 0.5 | 0.5 |
| B1 | SODIUM CITRATE | 0.2 | 0.2 | 0.2 | 0.2 | 0.2 |
| B1 | DISODIUM EDTA | 0.1 | 0.1 | 0.1 | 0.1 | 0.1 |
| B1 | SODIUM HYDROXIDE | 0.05 | 0.05 | 0.05 | 0.05 | 0.05 |
| B2 | TEREPHTHALYLIDENE DICAMPHOR SULFONIC ACID [ECAMSULE] | 3 | | | 3 | |
| B2 | BENZOPHENONE-4 | | | | | 5 |
| B2 | PHENYLBENZIMIDAZOLE SULFONIC ACID [ENSULIZOLE] | 3 | 4 | 4 | 5 | 4 |
| B2 | WATER | 7.2 | 7.2 | 7.2 | 12 | 20 |
| B2 | TRIETHANOLAMINE | 1.8 | 0 | 0 | 1.8 | 2.5 |
| B2 | SODIUM HYDROXIDE | 0.44 | 0.58 | 0.58 | 0.44 | |
| C | POLYMETHYLSILSESQUIOXANE | 0.5 | 0.5 | 0.5 | 0.5 | 0.5 |
| | Total (%) | 100 | 100 | 100 | 100 | 100 |
| | Brookfield Viscosity (cp): | 46,000 | 33,000 | 61,000 | 58,000 | 41,000 |
| | Total Oil Phase (%) | 12 | 12 | 12 | 12 | 12 |
| | Total Water Phase (%) | 88 | 88 | 88 | 88 | 88 |
| | Ratio (Water Phase/Oil Phase)*: | 7.33 | 7.33 | 7.33 | 7.33 | 7.33 |
| | Water Releasing Effect: | 3 to 4 | 4 | 4 | 4 to 5 | 4 |
| | Texture/Appearance: | Translucent to opaque, light yellow to white, gel-like cream | | | | |
| | Stability Results: | Emulsions remained stable after 12 weeks. No crystals formed. | | | | |

*Excludes powder (Phase C)

In making each of the examples in Table 1, the following procedure is used.

The ingredients of Phase B (aqueous) are mixed together in a side beaker with a rotor/stator mixer until all solids are dissolved, giving a clear solution. If needed, Phase B (aqueous) can be gently heated to about 40-45° C. until all solids are dissolved. The ingredients of Phase A (oil phase) are placed in a main beaker and are mixed well with a propeller mixer at about 600-700 RPM and set aside. The mixture of aqueous phase ingredients (Phase B) are slowly added to the mixed ingredients of Phase A (oil phase) using a propeller mixer over a period of 10-15 minutes for an about 1 kg batch. As the viscosity of the mixture increases, the stirring speed is increased from 700 rpm to about 1200 rpm. As the aqueous phase is mixed into the oil phase a water-in-oil emulsion is formed. Optionally, powders are added to the batch and are mixed into the water-in-oil emulsion.

TABLE 2

Example 6 (Comparative)

| Phase | US INCI Name | Ex. 6 |
|---|---|---|
| A | OCTOCRYLENE | 7 |
| A | ETHYLHEXYL SALICYLATE [OCTISALATE] | 5 |
| A | BUTYL METHOXYDIBENZOYLMETHANE [AVOBENZONE] | 3 |
| A | DIMETHICONE (and) DIMETHICONE/PEG-10/15 CROSSPOLYMER [KSG-210] | 5 |
| A | CETYL PEG/PPG-10/1 DIMETHICONE [ABIL EM 90] | 1 |
| B | WATER, PRESERVATIVES | 59.65 |
| B | GLYCERIN | 15 |
| B | PROPANEDIOL | 3 |
| B | SODIUM CHLORIDE | 0.5 |
| B | SODIUM CITRATE | 0.2 |
| B | DISODIUM EDTA | 0.1 |
| B | SODIUM HYDROXIDE | 0.05 |
| C | POLYMETHYLSILSESQUIOXANE [TOSPEARL 145 A] | 0.5 |
| | Total (%) | 100 |
| | Brookfield Viscosity (cp): | NA |
| | Total Oil Phase (%) | 21 |
| | Total Water Phase (%) | 79 |
| | Ratio (Water Phase/Oil Phase)*: | 3.76 |
| | Water Releasing Effect: | NA |
| | Texture/Appearance: | Thick, white cream |
| | Stability Results: | Not stable. Phase separated |

*Excludes powders (Phase C).

The comparative Example 6 was prepared by heating water phase and oil phase separately to 80° C. The water phase was added to the oil phase while mixing until homogeneous. The resulted emulsion was cooled to about room temperature. Optionally, powders were added and mixed well.

Similar to the inventive examples 1-5, the water-in-oil emulsion of Example 6 used emulsifying siloxane elastomer (KSG-210) as the primary emulsifier and an alkyl-substituted polyether dimethicone copolymer (Abil EM90) as the co-emulsifier. Organic UV filters were added to the oil phase to make ma sunscreen emulsion. Example 6 includes about 7% by weight octylcrylene, about 5% octisalate and about 3% avobenzone. The emulsion in Example 6 was formed initially as a thick, white cream, but its phases separated the following day. Thus, it was not possible to measure its "water-releasing" effect, nor its viscosity.

TABLE 3

Example 7 (Comparative)

| Phase | INCI Name | Ex. 7 |
|---|---|---|
| A | Dimethicone (and) Dimethicone/PEG-10/15 Crosspolymer (KSG-210) | 4 |
| A | Dimethicone (and) Dimethiconol (88/12) | 1 |
| A | Dimethicone | 6 |
| A | Trisiloxane | 16 |
| B | Water | 59.3 |
| B | Phenoxyethanol | 0.6 |
| B | Caprylyl glycol | 0.2 |
| B | Hexylene glycol | 0.1 |
| B | Iodopropynyl Butylcarbamate (10%) | 0.1 |
| B | Polyaminopropyl Biguanide (20% in water) | 0.2 |
| B | Butylene glycol | 2 |
| B | Glycerin | 10 |
| B | Sodium Citrate | 0.5 |
| | Total (%) | 100 |
| | Brookfield Viscosity (cp) | 5000 |
| | Total Oil Phase (%) | 27 |
| | Total Water Phase (%) | 73 |
| | Ratio (water phase/oil phase) | 2.7 |
| | Water Releasing Effect | 1 |
| | Texture: Translucent, milky serum; watery on skin upon application. No "water-beading/releasing" effect. | |
| | Microscope: Unstable. W/Si with leaking border, indicating potential instability of emulsion. | |

In making comparative Example 7, the following procedure was used. The ingredients of Phase B (aqueous) are mixed in together in a side breaker using a stirring bar to mix well and dissolve all solids. The ingredients of Phase A (oil phase) are placed in a main beaker and mixed well with a propeller mixer at about 600-700 RPM and set aside. The mixture of aqueous phase ingredients (Phase B) are slowly added to the mixed ingredients of Phase A using a prop mixer over a period of 10-15 minutes for a 1 kg batch. As viscosity slowly increased, the stirring speed is increased from 700 RPM to 1000 RPM to form a serum.

Comparative Example 7, in contrast to the present disclosure, has a total weight percentage of the aqueous phase or water phase of about 73% and a total weight percentage of oil of about 27%, making the ratio of the aqueous phase to oil phase about 2.7. Comparative Example 7 forms a translucent, milky serum that is watery on skin upon application. The viscosity of comparative Example 7 is measured using a Brookfield Viscometer, using spindle T-D and speed set at 10 rpm for 1 minute. The viscosity of comparative Example is about 5,000 cp (mPa·s). The water-releasing effect of comparative Example 7 is measured by placing about 0.2 g of the cosmetic composition on the back of a hand, then applying thereon by circling gently with the middle finger and ring finger of the other hand. No bead-like droplets having an average diameter of more than or equal to 1 mm appeared. The water-releasing effect of the serum of comparative Example 7 is about 1; therefore, comparative Example 7 has no water-releasing effect.

Comparative Example 7 is generally unstable. The microscope shows that the W/Si boundary has a leaking border, indicating potential instability of emulsion. Though the serum of comparative Example 7 initially forms as an emulsion, after 3 days of freeze-thaw cycles, the serum completely separates.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition comprising:
   (a) an aqueous phase containing at least one water-soluble UV sunscreen filter; and
   (b) an oil phase consisting of:
      (i) dimethicone, at a concentration by weight of from about 1% to about 25%, based upon weight of the composition; and
      (ii) an emulsifying crosslinked siloxane elastomer at a concentration, by weight, of about 0.5% to about 7%, based upon weight of the composition;
   wherein a phase ratio of the aqueous phase to the oil phase is from about 3.0 to about 12.0; and wherein the composition converts from an emulsion to a plurality of droplets upon application of shear.

2. The composition of claim 1 wherein the at least one water soluble UV filter is present in the composition in amount of from about 2% to about 25% by weight, based on the total weight of the composition.

3. The composition of claim 1 wherein the at least one water soluble UV filter is present in the composition in amount of from about 3% to about 20% by weight, based on the total weight of the composition.

4. The composition of claim 1 wherein the at least one water soluble UV filter is present in the composition in amount of from about 4% to about 18% by weight, based on the total weight of the composition.

5. The composition of claim 1 wherein the at least one water soluble UV filter is present in the composition in amount of from about 4% to about 15% by weight, based on the total weight of the composition.

6. The composition of claim 1 wherein the at least one water soluble UV filter is present in the composition in amount of from about 5% to about 10% by weight, based on the total weight of the composition.

7. The composition of claim 1, wherein the at least one water-soluble UV sunscreen filter is chosen from terephthalylidene dicamphor sulfonic acid (Ecamsule), phenylbenzimidazole sulfonic acid (Ensulizole), Benzophenone-4, aminobenzoic acid (PABA), camphor benzalkonium methosulfate, methylene bis-benzotriazolyl tetramethylbutylphenol (Bisoctrizole), disodium phenyl dibenzimidazole tetrasulfonate (Bisdisulizole disodium), tris-biphenyl triazine; their derivatives and corresponding salts; naphthaline bisimide derivatives, and cinnamido amine cationic quaternary salts and derivatives, and mixtures thereof.

8. The composition of claim 7 wherein the at least one water-soluble UV sunscreen filter is chosen from terephthalylidene dicamphor sulfonic acid (Ecamsule), phenylbenzimidazole sulfonic acid (Ensulizole), Benzophenone-4, and mixtures thereof.

9. The composition of claim 1, wherein the emulsifying crosslinked siloxane elastomer comprises a substituted or unsubstituted dimethicone/copolyol crosspolymer.

10. The composition of claim 9, wherein the emulsifying crosslinked siloxane elastomer is dimethicone/PEG-10/15 crosspolymer.

11. The composition of claim 1, wherein the emulsifying crosslinked siloxane elastomer is chosen from a substituted or unsubstituted dimethicone/polyglyceryl crosspolymer.

12. The composition of claim 11, wherein the emulsifying crosslinked siloxane elastomer is dimethicone/polyglycerin-3 crosspolymer.

13. The composition of claim 1, wherein the ratio of the aqueous phase to the oil phase is from about 4.0 to about 10.0.

14. The composition of claim 1, further including a powder at a concentration by weight of from about 0.1% to about 5%, based upon weight of the composition.

15. A composition comprising:
(a) an aqueous phase containing at least one water-soluble UV sunscreen filter chosen from terephthalylidene dicamphor sulfonic acid (Ecamsule), phenylbenzimidazole sulfonic acid (Ensulizole), and Benzophenone-4, at a concentration by weight of from about 4% to about 10%; based upon weight of the composition, wherein the aqueous phase is at a concentration by weight of from about 75% to about 90%, based upon weight of the composition; and
(b) an oil phase consisting of:
(i) dimethicone at a concentration by weight of from about 4% to about 20%, based upon weight of the composition; and
(ii) an emulsifying crosslinked siloxane elastomer at a concentration by weight of from about 1% to about 5%, based upon weight of the composition; wherein the composition converts from an emulsion to a plurality of droplets upon application of shear.

16. A process for inhibiting UV rays from contacting a surface comprising the steps of:
(1) providing a composition comprising:
(a) an aqueous phase containing at least one water-soluble UV sunscreen filter; and
(b) an oil phase consisting of:
(i) dimethicone, at a concentration by weight of from about 1% to about 25%, based upon weight of the composition; and
(ii) an emulsifying crosslinked siloxane elastomer at a concentration, by weight, of about 0.5% to about 7%, based upon weight of the composition;
wherein a phase ratio of the aqueous phase to the oil phase is from about 3.0 to about 12.0; and wherein the composition converts from an emulsion to a plurality of droplets upon application of shear;
(2) applying the composition onto the surface; and
(3) applying shear onto the composition, thereby transforming the composition into a plurality of droplets containing at least one water-soluble UV sunscreen.

17. The composition of claim 13, wherein the ratio of the aqueous phase to the oil phase is from 5.0 to about 9.0.

18. The composition of claim 17, wherein the ratio of the aqueous phase to the oil phase is 7.33.

19. The composition of claim 15, wherein the ratio of the aqueous phase to the oil phase is 7.33.

20. A composition comprising:
(a) an aqueous phase containing at least one water-soluble UV sunscreen filter; and
(b) an oil phase consisting of:
(i) dimethicone, at a concentration by weight of from about 1% to about 25%, based upon weight of the composition;
(ii) an emulsifying crosslinked siloxane elastomer at a concentration, by weight, of about 0.5% to about 7%, based upon weight of the composition, the emulsifying crosslinked siloxane elastomer selected from the group consisting of dimethicone/PEG-10/15 crosspolymer, dimethicone/polyglycerin-3 crosspolymer, and a combination thereof;
wherein a phase ratio of the aqueous phase to the oil phase is from about 3.0 to about 12.0; and
wherein the composition converts from an emulsion to a plurality of droplets upon application of shear.

21. A composition comprising:
(a) an aqueous phase containing at least one water-soluble UV sunscreen filter; and
(b) an oil phase consisting of:
(i) dimethicone, at a concentration by weight of from about 1% to about 25%, based upon weight of the composition; and
(ii) an emulsifying crosslinked siloxane elastomer at a concentration, by weight, of about 0.5% to about 7%, based upon weight of the composition; and
(iii) a co-emulsifier at a concentration, by weight, of about 0.01% to about 1%, based upon weight of the composition, the co-emulsifier chosen from PEG 10 dimethicone, PEG-9 polydimethylsiloxyethyl dimethicone and PEG-9, lauryl PEG-9 polydimethylsiloxyethyl dimethicone, dimethicone and PEG/PPG-18/18 dimethicone, and combinations thereof;
wherein a phase ratio of the aqueous phase to the oil phase is from about 3.0 to about 12.0; and
wherein the composition converts from an emulsion to a plurality of droplets upon application of shear.

* * * * *